US009119831B2

(12) United States Patent
Kentner et al.

(10) Patent No.: US 9,119,831 B2
(45) Date of Patent: Sep. 1, 2015

(54) METHODS OF MANUFACTURING BIOACTIVE GELS FROM EXTRACELLULAR MATRIX MATERIAL

(71) Applicant: ACell, Inc., Columbia, MD (US)

(72) Inventors: Kimberly A. Kentner, Columbia, MD (US); Katherine A. Stuart, Columbia, MD (US); Abram D. Janis, Columbia, MD (US)

(73) Assignee: ACell, Inc., Columbia, MD (US)

( * ) Notice: Subject to any disclaimer, the term of this patent is extended or adjusted under 35 U.S.C. 154(b) by 0 days.

(21) Appl. No.: 14/332,465

(22) Filed: Jul. 16, 2014

(65) Prior Publication Data

US 2014/0342007 A1 Nov. 20, 2014

Related U.S. Application Data

(63) Continuation of application No. 14/174,980, filed on Feb. 7, 2014, now Pat. No. 8,802,436.

(60) Provisional application No. 61/762,437, filed on Feb. 8, 2013.

(51) Int. Cl.
| | | |
|---|---|---|
| C12N 5/00 | (2006.01) | |
| C12N 5/02 | (2006.01) | |
| A61K 35/37 | (2015.01) | |
| A61K 35/38 | (2015.01) | |
| A61K 35/407 | (2015.01) | |
| A61K 35/22 | (2015.01) | |
| A61L 27/36 | (2006.01) | |
| A61L 27/52 | (2006.01) | |
| A61L 27/54 | (2006.01) | |
| A61K 9/00 | (2006.01) | |
| A61K 35/12 | (2015.01) | |
| A61K 38/18 | (2006.01) | |

(52) U.S. Cl.
CPC ............... *A61K 35/22* (2013.01); *A61K 9/0024* (2013.01); *A61K 35/12* (2013.01); *A61K 38/18* (2013.01); *A61K 38/1825* (2013.01); *A61K 38/1866* (2013.01); *A61L 27/3633* (2013.01); *A61L 27/3683* (2013.01); *A61L 27/3687* (2013.01); *A61L 27/52* (2013.01); *A61L 27/54* (2013.01); *A61L 2300/414* (2013.01)

(58) Field of Classification Search
CPC ... A61K 35/12; A61K 2300/00; A61K 38/00; A61K 31/65; A61K 35/38; A61K 31/715; A61K 38/39; A61K 38/488; A61K 31/00; A61K 35/35; A61K 45/06; A61K 9/0019; A61K 9/06; A61F 2002/30062; A61F 2002/30754; A61F 2210/0004; A61F 2/2418
See application file for complete search history.

(56) References Cited

U.S. PATENT DOCUMENTS

| | | | |
|---|---|---|---|
| 4,902,508 A | 2/1990 | Badylak et al. | |
| 4,956,178 A | 9/1990 | Badylak et al. | |
| 5,554,389 A | 9/1996 | Badylak et al. | |
| 5,573,784 A | 11/1996 | Badylak et al. | |
| 5,800,537 A | 9/1998 | Bell | |
| 6,576,265 B1 | 6/2003 | Spievack | |
| 6,579,538 B1 | 6/2003 | Spievack | |
| 8,361,503 B2 | 1/2013 | Badylak et al. | |
| 8,802,436 B1 | 8/2014 | Kentner et al. | |
| 2003/0216812 A1 | 11/2003 | Badylak | |
| 2007/0014773 A1* | 1/2007 | Matheny et al. | ........... 424/93.21 |
| 2007/0027460 A1 | 2/2007 | Case et al. | |
| 2007/0082060 A1 | 4/2007 | Hiles et al. | |
| 2007/0269476 A1 | 11/2007 | Voytik-Harbin et al. | |
| 2008/0107750 A1 | 5/2008 | Hodde et al. | |
| 2008/0181950 A1* | 7/2008 | Bates et al. | ................... 424/484 |
| 2008/0260831 A1* | 10/2008 | Badylak et al. | ............... 424/484 |
| 2010/0196480 A1 | 8/2010 | Hiles et al. | |
| 2011/0020418 A1 | 1/2011 | Bosley et al. | |
| 2011/0293667 A1 | 12/2011 | Baksh et al. | |
| 2014/0227364 A1 | 8/2014 | Kentner et al. | |

FOREIGN PATENT DOCUMENTS

| | | |
|---|---|---|
| WO | 2008/060377 | 5/2008 |
| WO | 2009/086499 | 7/2009 |

OTHER PUBLICATIONS

U.S. Appl. No. 14/174,980, filed Feb. 7, 2014, Kentner et al.
U.S. Appl. No. 14/174,996, filed Feb. 7, 2010, Kentner et al.
DeQuach et al., "Injectable Skeletal Muscle Matrix Hydrogel Promotes Neovascularization and Muscle Cell Infiltration in a Hindlimb Ischemia Model," European Cells and Materials 23:400-412 (2012).
French et al., "A naturally derived cardiac extracellular matrix enhances cardiac progenitor cell behavior in vitro," Acta Biomaterilia 1-8 (2012).
Freytes et al., "Preparation and rheological characterization of a gel form of the porcine urinary bladder matrix," Biomaterials 1-8 (2008).
Gilbert et al., "Production and characterization of ECM powder: implications for tissue engineering applications," Biomaterials 26:1431-1435 (2005).
Hong et al., "Mechanical properties and in vivo behavior of a biodegradable synthetic polymer microfiber—extracellular matrix hydrogel biohybrid scaffold," Biomaterials 32(13):1-16 (2011).
Johnson, et al., "Tailoring material properties of a nanofibrous extracellular matrix derived hydrogel," Nanotechnology 22:1-10 (2011).
Kentner et al., "Differential Release of Growth Factors from MatriStem® Urinary Bladder Matrix (UBM) Products," Society for Biomaterials Fall Symposium, New Orleans LA 1 page (2012).

(Continued)

*Primary Examiner* — Chris R Tate
*Assistant Examiner* — Douglas F White
(74) *Attorney, Agent, or Firm* — Burns & Levinson LLP

(57) ABSTRACT

The present invention is directed to methods of manufacturing bioactive gels from ECM material, i.e., gels which retain bioactivity, and can serve as scaffolds for preclinical and clinical tissue engineering and regenerative medicine approaches to tissue reconstruction. The manufacturing methods take advantage of a new recognition that bioactive gels from ECM material can be created by digesting particularized ECM material in an alkaline environment and neutralizing to provide bioactive gels.

16 Claims, 2 Drawing Sheets

(56) References Cited

OTHER PUBLICATIONS

Kentner et al., "Quantification of FGF-2, VEGF, & GAGs in MatriStem MicroMatrix UBM Biomaterial," BMES Fall Meeting, Hartford, CT 1 page (2011).

Kimmel et al., "The Clinical Effectiveness in Wound Healing With Extracellular Matrix Derived From Porcine Urinary Bladder Matrix: A Case Series on Severe Chronic Wounds," Journal of the American College of Certified Wound Specialists 2(3):55-59 (2010).

Seif-Naraghi et al., "Design and Characterization of an Injectable Pericardial Matrix Gel: A Potentially Autologous Scaffold for Cardiac Tissue Engineering," Tissue Engineering: Part A 16(6):2017-2027 (2010).

Sief-Naraghi et al., "Injectable extracellular matrix derived hydrogel provides a platform for enhanced retention and delivery of a heparin-binding growth factor," Acta Biomaterialia 8:3695-3703 (2012).

Seif-Naraghi et al., "Patient-to-Patient Variability in Autologous Pericardial Matrix Scaffolds for Cardiac Repair," J. of Cardiovasc. Trans. Res. 4:545-556 (2011).

Singelyn et al., "Catheter-Deliverable Hydrogel Derived From Decellularized Ventricular Extracellular Matrix Increases Endogenous Cardiomyocytes and Preserves Cardiac Function Post-Myocardial Infarction," Journal of the American College of Cardiology 59(8):751-763 (2012).

Singelyn et al., "Naturally derived myocardial matrix as an injectable scaffold for cardiac tissue engineering," Biomaterials 30:5409-5416 (2009).

Young et al., "Injectable Hydrogel Scaffold from Decellularized Human Lipoaspirate," Acta Biomater. 7(3):1040-1049 (2011).

International Search Report and Written Opinion for International Application No. PCT/US2014/015214, mailed May 8, 2014 (12 pages).

* cited by examiner

METHODS OF MANUFACTURING BIOACTIVE GELS FROM EXTRACELLULAR MATRIX MATERIAL

CROSS REFERENCE TO RELATED APPLICATIONS

This application claims priority to and benefit of U.S. Provisional Application No. 61/702,437, filed Feb. 8, 2013, the entire contents of which are incorporated by reference herein for all purposes.

GOVERNMENT SUPPORT

This invention was supported by grant no. NCC 9-58 from the National Space Biomedical Research Institute through NASA. The Government has certain rights in the invention.

TECHNICAL FIELD OF THE INVENTION

The present invention is related to methods of manufacturing bioactive gels from extracellular matrix material and their uses for restoration of tissues in a patient.

BACKGROUND

Biologic scaffolds composed of extracellular matrix material (ECM) have been used for the repair of variety of tissues including the lower urinary tract, esophagus, myocardium and musculotendinous tissues, often leading to tissue-specific constructive remodeling with minimal or no scar tissue formation.

Although uses of ECM as scaffolds for preclinical and clinical tissue engineering and regenerative medicine approaches to tissue reconstruction are very promising, challenges remain in the process to manufacture bioactive gels from ECM, which retain their bioactivity.

The methods of manufacturing bioactive gels from ECM described in the prior art require the use of enzymes and are time consuming because they require aggressive purification steps, which may lead to depletion in the bioactivity of the gels and may present additional regulatory barriers to marketing.

Thus, a need exists to manufacture bioactive gels from ECM which avoids cumbersome preparation and purification steps yet result in gels that retain the bioactivity of the original material.

SUMMARY OF THE INVENTION

The present invention generally pertains to improved methods of manufacturing bioactive gels from ECM which retain sufficient bioactivity to positively assist in tissue repair. The present invention utilizes reagents that do not introduce additional regulatory burdens far market approval or clearance of the gel invention. Thus, the invention describes methods of manufacturing bioactive gels from an ECM comprising (a) providing the ECM from one or more of the group consisting of but not limited to small intestine submucosa (SIS), urinary bladder submucosa (UBS), urinary bladder matrix (UBM) (includes epithelial basement membrane), porcine dermis (PD), and liver basement membrane (LBM), (b) particularizing the ECM to a particle size in the range of about 1 µm to about 1000 µm, (c) solubilizing concentrations in the range of about 0.5 to 11% weight/volume (w/v) of particularized powder in sodium hydroxide (NaOH) in the range of 0.1 to 1.0 M for periods of time ranging from about 1 hour to about 48 hours at 4° C., (d) neutralizing the solubilized ECM prepared in step (c) with hydrochloric acid (HCl), optionally equimolar relative to NaOH, ranging from 0.1 to 1M to form the gel, and (e) optionally, freezing the neutralized solubilized ECM prepared in step (d), optionally (f) lyophilizing the frozen ECM prepared in step (e), and optionally (f) reconstituting the lyophilized gel in water or saline.

The advantages provided by the methods of manufacturing bioactive gels in the above manner are that aggressive purification steps, which are deleterious to bioactivity, tedious to perform or are time consuming, and which increase the regulatory burden (e.g. FDA approval), are avoided.

DETAIL DESCRIPTION

Figure 1:
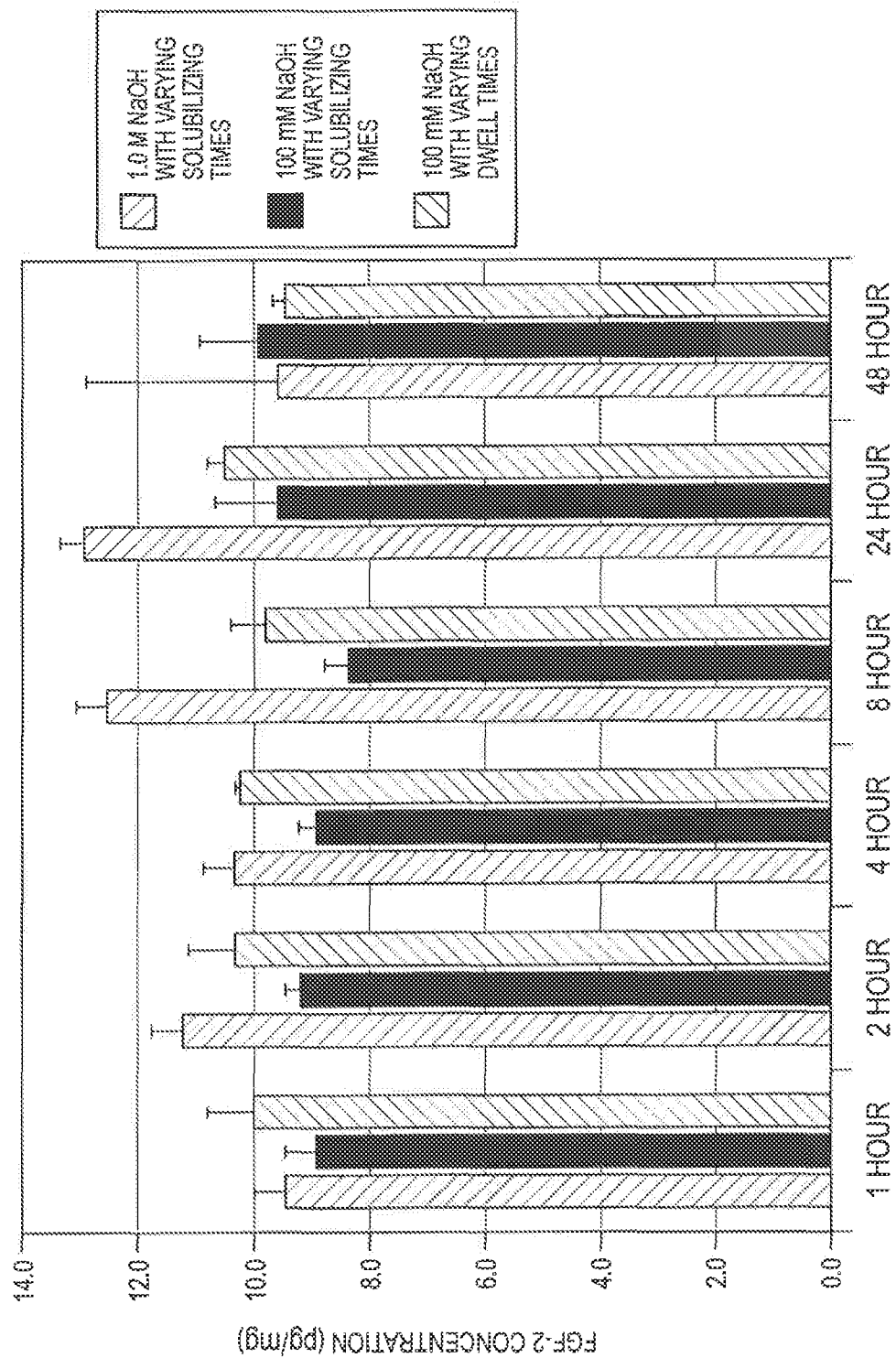
FIG. 1 shows the FGF-2 content (pg/mg) of gels following various solubilization conditions in NaOH according to embodiments of the invention. All gels not marked with a % w/v were done at 7.0% w/v UBM to NaOH. All gels in FIG. 1 were done at 7.0% w/v UBM to NaOH.

The present invention is directed to methods of manufacturing bioactive gels from ECM, i.e., gels which retain sufficient bioactivity to positively assist tissue repair by decreasing the time needed for repair, decreasing scar tissue formation, and improving restoration of the injured tissue to its pre-damaged native structure and function as compared to injured tissues not treated with the bioactive gel according to the invention. The gel invention and methods of making described herein serves as scaffolds for preclinical and clinical tissue engineering and regenerative medicine approaches to tissue reconstruction. Bioactivity in the ECM gel according to the invention is in the range of about 0 to 100%, 25-75%, 10-25%, less than 10%, less than 5% or less than 1% of the bioactivity of one or more bioactive molecules in the native ECM from which the gel was derived. As will be described in detail below, these manufacturing methods take advantage of a new recognition that bioactive gels from ECM can be created by solubilizing a particularized ECM in a basic (greater than pH 7) environment, which when neutralized with acid provides bioactive gels.

In accordance with the inventive methods, the ECM may be derived from layers of native mammalian tissues including but not limited to submucosa, dermis, epithelial basement membrane, or from tissues such as aponeurosis, fascia, tendon, ligament, smooth and skeletal muscle and treatment site-specific. ECM. The native mammalian tissue source may be porcine, bovine, ovine, allogenic, autogenic, for example. For example, the ECM may be SIS (small intestinal submucosa), UBS (urinary bladder submucosa) or UBM (urinary bladder matrix) or liver basement membrane (LBM) described in U.S. Pat. No. 6,576,265, U.S. Pat. No. 6,579,538, U.S. Pat. No. 5,573,784, U.S. Pat. No. 5,554,389, U.S. Pat. No. 4,956,178, and U.S. Pat. No. 4,902,508, each of which are incorporated by reference herein. In one embodiment of the invention, the ECM is derived from a mammalian tissue and comprises bioactive components of the extracellular matrix material that are arranged and in quantities similar to those in the tissue in its native form.

In accordance with the inventive method, the ECM derived from any one of the above sources is particularized, i.e., the size of the ECM particles are in a range of about 1 μm to about 1000 μm. In one embodiment, particularization of the ECM prior to subjecting the ECM to a basic environment provides homogeneity to the ECM, provides a more uniform composition in comparison to ECM from individual animals, decreasing the impact of inter-donor variability. In another embodiment, the particularization of the ECM facilitates in solubilizing the matrix in a basic environment by increasing surface area to volume ratio.

The particulate ECM product, e.g., particularized ECM, is manufactured by grinding/milling or otherwise performing a size reduction process to ECM typically but not exclusively originally provided in sheet form. The resulting particulate can be any desired range of density for example in the range of about $0.1 \text{ g/cm}^3$-$10 \text{ g/cm}^3$, about $0.10.1 \text{ g/cm}^3$-$1 \text{ g/cm}^3$ or about $1 \text{ g/cm}^3$, and particle size for example in the range of about 1 micron-1000 microns, about 200-700 microns, about 300-600 microns, or about 400 microns.

A basic environment is provided by solutions of alkaline compounds. Alkaline compounds which could be used in accordance with the invention are metal hydroxides which include, but are not limited to, LiOH, NaOH, KOH, RbOH, and CsOH. Alkaline compounds which could be used in accordance with the invention also include weak bases, such as but not limited to, ammonia ($NH_3$), pyridine ($C_5H_5N$), hydroxylamine ($H_2NOH$), methylamine ($NH_2CH_3$) and the like. Alkaline compounds are generally used at a concentration ranging from 0.1 Molar to 1.0 Molar, although concentrations lower that 0.1 Molar or higher than 1.0 Molar are also contemplated in an embodiment of the invention.

Concentrations of particularized ECM to NaOH (w/v) are in the range of 0.1% to about 20%, in particular 0.5% to 11%, and more particular, 7%.

The solubilization step at 4° C. (i.e., digestion) of the particularized ECM can extend over a period of time ranging from a few minutes to several hours (e.g., 30 minutes to 48 hours) or days (e.g., 3-7 days), 30 minutes to 12 hours, 12-24 hours, 24 to 36 hours, 36 to 48 hours, or two to seven days. In an embodiment of the invention, it is contemplated that the time period required for the digestion step is determined by the size of the particularized extracellular matrix material and/or the concentration of the metal hydroxide used for solubilization. For example, if the concentration of an alkaline compound, such as NaOH, is low, longer incubation, i.e., longer time period for solubilization may be required. After the solubilization step in a basic solution, the solubilized ECM (i.e., the gel form) is neutralized to a neutral pH using molar concentrations, e.g., equimolar concentrations of an acid in a volume sufficient for the solubilized ECM to reach pH 6.8 to 7.4. Acids, which aid in neutralization of the ECM gel, can be selected from weak or strong acids. Selectivity of acids for the neutralization step depends on the salts which are produced when an acids reacts with the basic environment during neutralization. The resulting salt should be biocompatible. For example, in an embodiment of the invention, hydrochloric acid (HCl) is used to neutralize the basic environment created by the base NaOH because the resulting salt (i.e., NaCl) is clinically acceptable.

Following neutralization, optionally, gels can be subjected to various dwell periods, 1-48 hours, 12-36 hours, or 36 to 48 hours to promote refolding of denatured bioactive components. Dwell periods are generally performed with or without shaking or stirring the gel in a cold room (i.e., at temperature of about 4° C.), alternatively at room temperature. Dwell periods could extend beyond 48 hours to a few days, for example, 3-7 days to promote restructuring of the gel.

According to the method of the invention, once the gel is neutralized it may optionally be subjected to one or more steps of freeze drying cycles to facilitate the conversion of the neutralized gel to a powder (having a neutral pH). The powder can be reconstituted into a gel without altering its bioactivity by mixing the powder with a liquid, such as water, or a buffer solution which maintains the neutral pH of the gel. In addition, preservation of bioactivity of ECMs may be achieved through lyophilization.

In one embodiment according to the invention, the freeze dried, solubilized ECM is reconstituted using water and two 3 mL syringes. One syringe contains the lyophilized gel, the other water, and they are mixed together via a connecter between the two syringes. The mixture is injected back and forth several times to achieve mixing. Various concentrations of ECM in NaOH can be tested for handling properties (i.e. injectability, tackiness, viscosity) to determine their ability to be applied using the two syringe system. The final consistency of all gels is foam-like, and each one adheres to the surface to which it is applied while also maintaining consistency, which may be desirable in zero gravity conditions, for example, in space. Accordingly, the gel invention may be used for tissue repair during space exploration.

In one embodiment, to the solubilized and neutralized ECM gel, particularized ECM is added, to increase the viscosity or the bioactivity of the gel. For example, UBM powder in the size range of about 1 micron-1000 microns, about 200-700 microns, about 300-600 microns, about 100 to 400 microns, about 200 microns or about 400 microns is added to a UBM gel prepared by the above methods to enhance the viscosity or the bioactivity of the gel, that is, the gel has better handling or the gel is made capable of producing a higher concentration of bioactive molecules, for example, growth factors, such as FGF, e.g., FGF-2, CTGF, or VEGF, ECM powder can be added, prior to, during, or after the gels are neutralized.

In a particular embodiment, 7.0% UBM to 100 mM NaOH solubilized at 4° C. is used to manufacture the bioactive gel. A dwell period may or may not be used. UBM powder may be added to the gel to increase viscosity and/or bioactivity.

EXEMPLIFICATIONS

For the following exemplifications, any number of ECM products such as but not limited to one or more of isolated urinary bladder submucosa, small intestinal submucosa, dermis, for example, could be used. In the following exemplifications, UBM, an ECM isolated from the urinary bladder and having epithelial basement membrane is used as an exemplary ECM. However the invention disclosed herein is not limited to UBM and is applicable to any isolated ECM.

In an exemplification, gels were created using various concentrations of particularized UBM (0.5-11% w/v) solubilized in various concentrations of NaOH (0.1-1.0M). UBM was solubilized for various time periods (1-48 hours) in its respective concentration of UBM and NaOH at 4° C. In order to test whether the UBM could restructure after solubilization, gels were also made using various dwell periods (1-48 hours) following neutralization.

Figure 2:
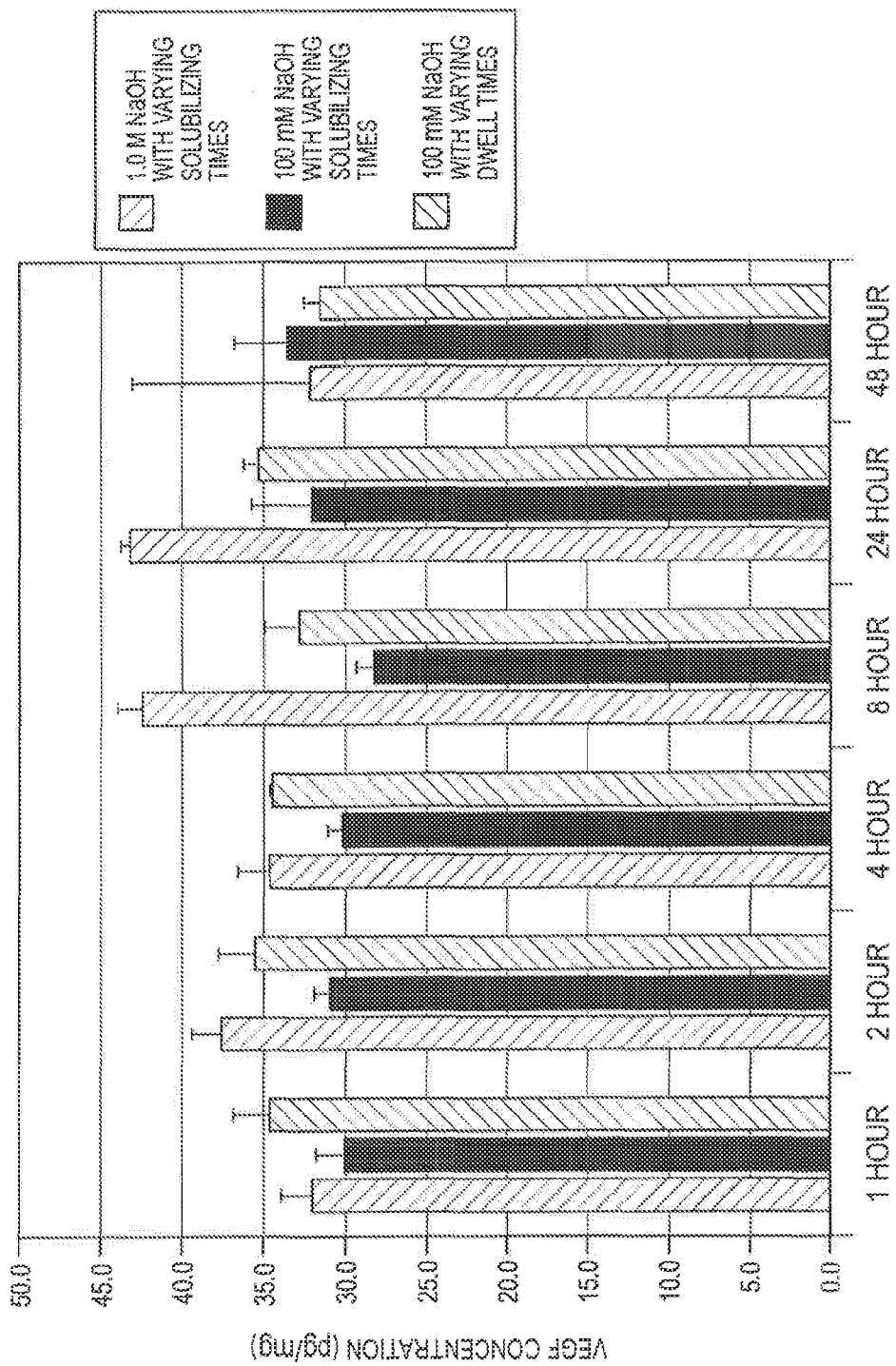
FIG. 2 shows the VEGF content (pg/mg) of gels following various solubilization conditions in NaOH according to embodiments of the invention. All gels not marked with a w/v were done at 7.0% w/v UBM to NaOH. All gels in FIG. 1 were done at 7.0% w/v UBM to NaOH.

UBM gels created in the above manner were tested in vitro for bioactive molecular content. In this study, growth factor (e.g., FGF-2, CTGF, VEGF) content was analyzed. Data for FGF-2 and VEGF content following solubilization for each gel structure is shown in FIGS. 1 and 2. Lower concentration gels (1-6%) are not shown but produced similar results. As shown in FIGS. 1 and 2, FGF-2 and VEGF, particularly VEGF levels increased in these studies.

In one study it was found that using 7.0% w/v UBM to various range of NaOH with 24 hours of solubilizing at 4° C. and no dwell period had significantly influenced the FGF-2 and VEGF contents in the gel. FGF-2 and VEGF contents were measure by standard ELISA procedures.

What is claimed is:

1. A bioactive wound healing material, comprising:
a gelled extracellular matrix material in a basic solution wherein the extracellular matrix material is derived from the extracellular matrix of a mammal and comprises a concentration of ECM to a base (w/v) in the range of 0.1% to about 20%, wherein said wound healing material is gelled at room temperature.

2. The bioactive wound healing material of claim 1 wherein the base comprises NaOH.

3. The bioactive wound healing material of claim 1 wherein said wound healing material is lyophilized.

4. The bioactive wound healing material of claim 3 wherein said lyophilized material is reconstituted in a solution.

5. The bioactive wound healing material of claim 1 wherein said gelled extracellular matrix material comprises epithelial basement membrane (UBM).

6. The bioactive wound healing material of claim 2 wherein said base comprises 0.1-1.0M NaOH.

7. The bioactive wound healing material of claim 1 wherein said base is selected from the group consisting of LiOH, NaOH, KOH, RbOH, CsOH $NH_3$, $C_5H_5N$, $H_2NOH$, and $NH_2CH_3$.

8. The bioactive wound healing material of claim 1 further comprising a bioactive component selected from the group consisting of VEGF, FGF-2, CTGF, and combinations thereof.

9. The bioactive wound healing material of claim 1 wherein the extracellular matrix material comprises submucosa.

10. The bioactive wound healing material of claim 1 wherein the extracellular matrix material is selected from the group consisting of submucosa, tunica propria, dermis, and liver basement membrane.

11. The bioactive wound healing material of claim 2 wherein the concentration of ECM to NaOH (w/v) is in the range of 0.5% to 11%.

12. The bioactive wound healing material of claim 2 wherein the concentration of ECM to NaOH (w/v) is 7%.

13. The bioactive wound healing material of claim 1 further comprising powdered ECM comprising a particle size of about 1 micron to about 1000 microns.

14. The bioactive wound healing material of claim 1 further comprising powdered ECM comprising a particle size in the range of about 200 microns to 700 microns or about 300 microns to 600 microns.

15. The bioactive wound healing material of claim 1 further comprising powdered ECM comprising a particle size in the range of about 100 microns to about 400 microns.

16. The bioactive wound healing material of claim 1 further comprising powdered ECM comprising a particle size in the range of about 200 microns to about 400 microns.

* * * * *